United States Patent

Broger et al.

[11] Patent Number: 5,880,285
[45] Date of Patent: Mar. 9, 1999

[54] PROCESS FOR MANUFACTURE OF OPTICALLY ACTIVE ISOCHINOLE COMPOUNDS

[75] Inventors: Emil Albin Broger, Magden; Michelangelo Scalone, Birsfelden; Christof Wehrli, Witterswil, all of Switzerland

[73] Assignee: Roche Vitamins Inc., Parsippany, N.J.

[21] Appl. No.: 993,299

[22] Filed: Dec. 18, 1997

[30] Foreign Application Priority Data

Dec. 23, 1996 [EP] European Pat. Off. .............. 96120844

[51] Int. Cl.$^6$ .................................................. C07D 217/20
[52] U.S. Cl. ............................................................ 546/149
[58] Field of Search ............................................. 546/140

[56] References Cited

U.S. PATENT DOCUMENTS

| | | | |
|---|---|---|---|
| 4,115,389 | 9/1978 | Monkovic | 260/285 |
| 4,727,147 | 2/1988 | Wintermeyer et al. | 546/149 |
| 4,857,648 | 8/1989 | Broger et al. | 546/149 |
| 4,954,644 | 9/1990 | Sayo et al. | 556/14 |
| 5,466,844 | 11/1995 | Spirdler et al. | 556/11 |

*Primary Examiner*—Zinna Northington Davis
*Attorney, Agent, or Firm*—George W. Johnston; Patricia S. Rocha-Tramaloni; Robert A. Silverman

[57] ABSTRACT

A process for the manufacture of optically active (R)- or (S)-1-(4-methoxy-benzyl)-1,2,3,4,5,6,7,8-octahydro-isoquinoline adducts of the formula

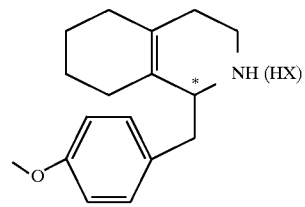

wherein
HX signifies a mineral acid from the group of $HBF_4$, $H_2SO_4$, $HPF_6$, HBr, HI, HCl, $HSbF_6$ or $HClO_4$, or a strong organic acid from the group of $C_{1-8}$-alkyl$SO_3H$, picric acid, formic acid, a lower alkylsulphonic acid or arylcarboxylic acid or a dicarboxylic acid,
from a compound of the formula

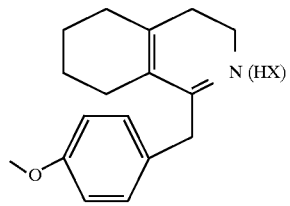

wherein HX has the significance given above, by asymmetric hydrogenation in the presence of a complex consisting of optically active diphosphine ligands with iridium, optionally in the presence of an additive.

12 Claims, No Drawings

PROCESS FOR MANUFACTURE OF OPTICALLY ACTIVE ISOCHINOLE COMPOUNDS

BACKGROUND

The asymmetric hydrogenation of carbon-nitrogen double bonds in imines is known. Rhodium, iridium or titanium catalysts (J. Mol. Catal. 1990, 62, 243; J. Am. Chem. Soc., 1994, 116, 8952 and J. Am. Chem. Soc., 1990, 112, 9400) have hitherto been used. The imines have always been used as the free base. Ruthenium catalysts are known for specially functionalized substrates (Tetrahedron Letters 1990, 31, 4117).

The hydrogenation of the compound of formula II (formula II described below) as the free base is problematical, since it is unstable in this form and disproportionates to the corresponding 1-(4-methoxy-benzyl)-5,6,7,8-tetrahydro-isoquinoline (tetrabase) and also to rac-1-(4-methoxy-benzyl)-1,2,3,4,5,6,7,8-octahydro-isoquinoline (rac-octabase). Moreover, the known processes such as for example the production of dextromethorphan have the disadvantage of racemate resolution, since the known hydrogenation of a compound of formula II (formula II described below) in the presence of a heterogeneous catalyst leads to a racemate, which must be resolved, since only the (S)-enantiomer of formula I (formula I described below) is used. Furthermore, the undesired (R)-enantiomer of the compound of formula I (described below) must be processed over several reaction steps, racemized and recycled.

The object of the present invention is to provide a process which permits the asymmetric hydrogenation of enimines in the form of their salts without the occurrence of the disadvantages described above.

SUMMARY OF THE INVENTION

The present invention relates to a catalytic process for the manufacture of optically active compounds of the formula

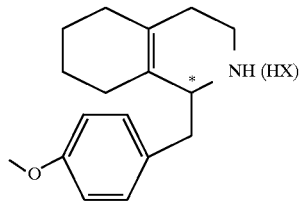

I wherein

HX is a mineral acid from the group of HBF$_4$, H$_2$SO$_4$, HPF$_6$, HBr, HI, HCl, HSbF$_6$ or HClO$_4$, or a strong organic acid from the group of C$_{1-8}$-alkylSO$_3$H, picric acid, formic acid, a lower alkylcarboxylic acid or arylcarboxylic acid, such as for example acetic acid, propionic acid or benzoic acid, or a dicarboxylic acid, such as for example oxalic acid, succinic acid, maleic acid or phthalic acid, starting from a compound of the formula

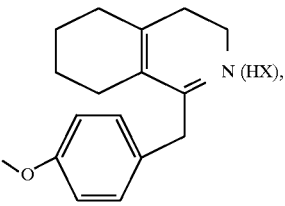

II wherein HX has the above significance.

DETAILED DESCRIPTION OF THE INVENTION

The process in accordance with the invention comprises asymmetrically hydrogenating a compound of the formula

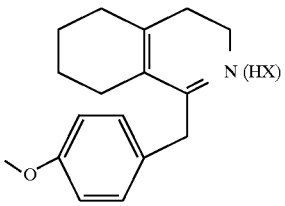

II in which HX has the above significance, to a compound of formula I in the presence of a complex of iridium with an optically active ligand and, if desired, in the presence of an additive.

The compounds of formulae I and II in which HX signifies HBF$_4$, H$_2$SO$_4$, HPF$_6$, HBr, HI, HSbF$_6$, HClO$_4$, or a strong organic acid from the group of C$_{1-8}$-alkylSO$_3$H, picric acid, formic acid, a lower alkylcarboxylic acid or arylcarboxylic acid, such as for example acetic acid, propionic acid or benzoic acid, or a dicarboxylic acid, such as for example succinic acid, maleic acid or phthalic acid, are also objects of the invention.

As optically active iridium complexes for the process in accordance with the invention their come into consideration especially optically active cationic, anionic and neutral iridium complexes of the formulas

| | |
|---|---|
| $[\text{Ir}(Y)(L_n)]^+ A^-$ | III-a |
| $[\text{Ir}(Y)(L_n)B]$ | III-b |
| $([\text{Ir}(Y)(B)_4])_o^- M^{r+}$ | III-c |
| $[\text{IrH}(Y)(B)_2]_2$ | III-e |
| $[\text{Ir}(Y)(B)_3]_2$ | III-f |
| $[\text{Ir}(B)_3(Y)]$ | III-g | wherein

L signifies a neutral ligand;
A signifies an anion of an oxygen acid or complex acid;
B signifies an anionic coordinating ligand;
n signifies 0, 1 or 2;
o signifies 1 or 2;
r signifies 1 or 2;
M$^+$ signifies alkali, alkaline earth or tetrasubstituted ammonium;

Y signifies a chiral diphosphine ligand of the formula

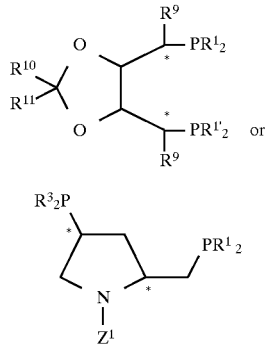

IV

V in which
R$^1$, R$^{1\prime}$ each independently signify C$_{3-8}$-cycloalkyl, aryl or heteroaryl or together with the phosphorus atom signify 9-dibenzophospholyl;
R$^2$ signifies C$_{1-8}$-alkyl, C$_{3-8}$-cycloalkyl, aryl or aralkyl; or two R$^2$'s together in the same molecule can form a 5- to 8-membered ring;
R$^3$ signifies C$_{1-8}$-alkyl, heteroaryl, aryl, C3–8-cycloalkyl or aralkyl;
R$^9$, R$^{10}$, R$^{11}$ each independently signify hydrogen, C$_{1-8}$-alkyl, halogenated C$_{1-8}$-alkyl, C$_{3-8}$-cycloalkyl, aryl or aralkyl; or R$^{10}$ and R$^{11}$ together can form a 5- to 8-membered ring; and
Z$^1$ signifies hydrogen, C$_{1-8}$-alkyl, aralkyl, —CO$_2$R$^2$, —CONR$^2{}_2$, —SO$_2$R$^{10}$, —POR$^{10}{}_2$ or —COR$^3$.

The optically active iridium complexes III-a to III-g are known and can be synthesized or produced in situ from the components in the absence or in the presence of the compounds of formula II to be hydrogenated.

The compounds of formula I in the form of their free bases are known and are intermediates for dextromethorphan. Compounds of formula I can be converted into dextromethorphan in a know manner, for example, in anology to the procedures described in Helvetica Chimica Acta 1950, 33, 1437, by N-acylation and subsequent cyclization with a strong acid to the corresponding morphinan derivative, cleavage of the acyl-group and N-methylation.

In connection with the compounds of formulas III-a to III-g and IV and V the following definitions of terms apply irrespective of whether the terms in question appear alone or in combination.

The term "neutral ligand" signifies in the scope of the present invention readily exchangeable ligands such as olefins, e.g. ethylene, propylene, cyclooctene, 1,5-hexadiene, norbornadiene, 1,5-cyclooctadiene, benzene, hexamethylbenzene, p-cymene and the like, nitriles such as acetonitrile and benzonitrile, or also solvent which is used such as e.g. THF, toluene etc. Where more than one such ligand is present, these can also be different from each other.

The term "halide" embraces fluorine, chlorine, bromine and iodine in the form of alkali, alkaline earth or tetrasubstituted ammonium compounds.

The term "anionic coordinating ligand" embraces e.g. halogen, a carboxylic acid residue, a sulphonate residue, such as e.g. tosylate or methanesulphonate, a 1,3-diketonate, such as e.g. acetylacetonate, an optionally substituted phenolate, hydroxy, nitrite, cyanate, rhodanide, cyanide, allyl and 2-methylallyl.

The term "oxygen acid or complex acid" signifies in the scope of the present invention acids from the group of H$_2$SO$_4$, HClO$_4$, HBrO$_4$, HIO$_4$, HNO$_3$, H$_3$PO$_4$, H$_3$PO$_3$, CF$_3$SO$_3$H or C$_6$H$_5$SO$_3$H as well as halogen complexes with the elements boron, phosphorus, arsenic, antimony or bismuth. HClO$_4$, CF$_3$SO$_3$H, HPF$_6$, HBF$_4$, HB(Ph)$_4$, HB(3,5-C$_6$H$_3$)$_4$, HSbF$_6$ and HAsF$_6$ are preferred representatives.

The term "C$_{1-8}$-alkyl" signifies in the scope of the present invention for all alkylene-containing systems hydrocarbons with 1 to 8 carbon atoms, i.e. straight-chain or branched alkyl groups, such as, for example, methyl, ethyl, propyl, isopropyl, butyl, isobutyl, tert.-butyl, pentyl, isopentyl, neopentyl, hexyl, tert.hexyl, heptyl, isoheptyl, octyl and isooctyl.

The term "C$_{1-8}$-alkoxy" signifies an alkyl group as defined above, which is bonded via an oxygen atom. Methoxy, ethoxy, propoxy, isopropoxy, butoxy and the like can be mentioned by way of example.

The term "C$_{3-8}$-cycloalkyl" signifies in the scope of the present invention cyclopropyl, cyclobutyl, cyclopentyl, cyclohexyl, cycloheptyl and cyclooctyl.

The term "halogenated alkyl" signifies in the scope of the present invention alkyl groups having a variable number of halogen atoms, especially chlorine or fluorine, preferably at least one halogen atom or, however, perfluorinated or perchlorinated compounds such as, for example, trifluoromethyl, trichloromethyl, pentafluoroethyl and the like.

The term "aryl" signifies phenyl residues which can be not only unsubstituted, but also mono-substituted in the ortho-, meta- or para- position or multiply-substituted. As substituents there come into consideration phenyl, C$_{1-8}$-alkyl or alkoxy groups, halogenated C$_1$–C$_{-8}$ alkyl, di-C$_1$–C$_8$-alkylamino, diphenylamino, dibenzylamino, morpholino, piperidino, pyrrolidino, halogen, trialkylsilyl, e.g. trimethylsilyl and the like. Moreover, the term can also signify naphthyl.

The term "aralkyl" signifies groups in which the aryl residue has the foregoing significance and the alkyl residue likewise has the significance set forth above. Benzyl and the like can be cited by way of example.

The term "heteroaryl" signifies five- or six- membered heteroaromatics, which additionally can have fused aromatic groups, containing or more hetero atoms from the group of nitrogen, oxygen and sulphur. The five-membered heteroaromatics pyrrole, thiophene and furan can be mentioned by way of example. Pyridine can be mentioned, for example, from the group of six-membered heteroaromatics. The heteroaromatics can be substituted in the same manner as the aryls set forth above, with the nitrogen atom of nitrogen-containing heteroaromatics additionally being optionally substituted with hydrogen or alkyl or alkoxy groups.

The ligands of formulas IV and V are compounds which are known and can be prepared, for example, as described in SYNLETT 1992, 169.

The compounds of formula II can be prepared in analogy to the method for preparation of isoquinoline derivatives described in Helvetica Chimica Acta 1961, 44, 1546 or according to the method described in EP 97116763.0.

The asymmetric hydrogenation in accordance with the invention of compounds of general formula II to compounds of general formula I is effected in suitable organic solvents which are inert under the reaction conditions. As such solvents there especially come into consideration lower alcohols, such as methanol, ethanol and isopropanol; esters; halogenated hydrocarbons, such as, for example, methylene chloride, chloroform and the like; hydrocarbons from the group of toluene, xylene and the like; ethers, such as, for example, tert-butyl methyl ether, diethyl ether, tetrahydrofuran, dioxan and furan; amides, such as dimethylformamide (DMF); nitriles, such as acetonitrile; carboxylic acids, such as acetic acid; and sulphoxides, such as dimethyl sulphoxide (DMSO). Further, mixtures of these solvents with one another or also with water can be used. Hydrocarbons, alcohols and water or mixtures thereof are preferred solvents. An especially preferred solvent mixture consists of an alcohol and hydrocarbons, such as toluene and methanol. An especially preferred solvent mixture of three solvents comprises toluene, methanol and water.

The process in accordance with the invention is preferably carried out in the presence of an additive in the form of a base. The bases are compounds from the group of carboxylic acid salts, such as for example sodium acetate, sodium formate and the like, primary, secondary and tertiary amines, such as, for example, diisopropylamine, triethylamine and diisopropyl-ethylamine, as well as diamines of the ethylenediamine and tetramethyl-ethylenediamine type or imides, such as succinimide and phthalimide, or alkalialkoholates, such as sodium methylate, or sodium hydroxide. (R or S)-1-(4-Methoxy-benzyl)-1,2,3,4,5,6,7,8 octahydro-isoquinoline can be mentioned as a further additive. Tertiary amines, such as diisopropylamine and triethylamine, are especially preferred. Carbonates, such as sodium hydrogen carbonate, sodium carbonate, potassium hydrogen carbonate and disodium hydrogen phosphate and the like are also preferred additives.

Both the enantiomeric purity and the yields are increased considerably by the addition of additives.

The amounts of additive used lie in the range of 0.001 to 100 mol equivalents based on the compounds of formulae II and, respectively, III-a to III-g.

If a base from the aforementioned group is used as the additive, its amount lies in the range of 0.001–100 mol equivalents, preferably in the range of 0.001–10 mol equivalents and particularly in the range of 0.001–2 mol equivalents, based on the compounds of formula II.

The anionic coordinating ligands in accordance with the definition set forth above can be included in the reaction mixture in amounts of 0.1–100 mol equivalents, preferably 0.5–50 mol equivalents and particularly 1–10 mol equivalents, based on the compounds of formula III-a to III-g.

According to a preferred embodiment of the asymmetric hydrogenation process, liquid or super-critical carbon dioxide is used as the solvent alone or in combination with other solvents set forth above. Even a small percentage content of carbon dioxide in the reaction mixture leads to an increase in yield of the product as will be evident from Examples 1.6 to 1.8 and Example 1.5 as a comparative example.

The salts of the compounds of formula II can be prepared in a manner known per se, e.g. starting from the known hydrochloride of formula II by salt exchange or by acid replacement. Thereby, the use of water and/or chlorinated solvents can be dispensed with.

The asymmetric hydrogenation is conveniently carried out at temperatures in the range of about 10° C. to about 200° C., preferably 10° C. to 100° C. and particularly 20° C. to 100° C., and under a pressure of about 1 to 250 bar, preferably 1 to 180 bar and particularly 10 to 90 bar.

The molar ratio of substrate to catalyst (S/C) between the compounds of formula II to be hydrogenated and the iridium complexes of formulae III-a to III-g is conveniently 20 to 80 000, preferably 100 to 50 000 and particularly 100 to 30 000.

Iridium complexes with optically active diphosphine ligands of formulas IV and V are used for the asymmetric hydrogenation of compounds of formula II.

Examples of especially preferred ligands of formulas IV and V are:

(2R,3R)-O-Isopropylidene-2,3-dihydroxy-1,4-bis-[bis-(4-methoxy-3,5-dimethylphenyl)phosphino]butane;

tert-butyl (2S ,4S )-4-(di-m-tolylphosphino)-2-[(di-m-tolylphosphino)methyl]-1-pyrrolidincarboxylate;

(2R,3R)-O-isopropylidene-2,3-dihydroxy-1,4-bis-[bis-(4-methoxy-3,5-diisopropyl-phenyl)phosphino]butane;

(2R,3R)-O-isopropylidene-2,3-dihydroxy-1,4-bis-[bis-(3,5-ditert-butylphenyl)phosphino]butane;

(2R,3R)-O-isopropylidene-2,3-dihydroxy-1,4-bis-[bis-(3,5-di-N-morpholinophenyl)phosphino]butane;

(2R,3R)-O-isopropylidene-2,3-dihydroxy-1,4-bis-[bis-(3,4,5-trimethoxyphenyl)phosphino]butane (2R,3R)-O-isopropylidene-2,3-dihydroxy-1,4-bis-[bis-(2-naphthyl)phosphino]butane;

(2R,3R)-O-isopropylidene-2,3-dihydroxy-1-(dicyclohexylphosphino)-4-[bis-(4-methoxy-3,5-ditert-butyl-phenyl)phosphino]butane;

(2R,3R)-O-isopropylidene-2,3-dihydroxy-1-(diphenylphosphino)-4-[bis-(4-methoxy-3,5-ditert-butyl-phenyl)phosphinolbutane;

(2R,3R)-O-isopropylidene-2,3-dihydroxy-1-(dicyclohexylphosphino)-4-[bis-(3,5-ditert-butyl-phenyl)phosphino]butane;

tert-butyl (2S,4S)-4-[bis-(4-methoxy-3,5-dimethyl-phenyl)phosphinol-2-[bis-(4-methoxy-3,5-dimethyl-phenylphosphino)methyl]-1-pyrrolidinecarboxylate;

tert-butyl (2S,4S)-4-[bis-(3,5-ditert-butyl-phenyl)phosphino]-2-[bis-(3,5-ditert.-butyl-phenylphosphino)methyl]-1-pyrrolidinecarboxylate;

tert-butyl (2S,4S)-4-[diphenyl)phosphino]-2-[bis-(3,5-ditert-butyl-phenyl-phosphino)methyl]-1-pyrrolidinecarboxylate; and tert-butyl (2S,4S)-4-[bis-(4-methoxy-3,5-ditert.-butyl-phenyl)phosphino]-2-[bis-(4-methoxy-3,5-ditert-butyl-phenylphosphino)methyl]-1-pyrrolidinecarboxylate.

The following Examples illustrate the invention and do not represent any limitation thereof. The abbreviations used in these Examples have the following significances:

| HPLC | High pressure liquid chromatography |
|------|-------------------------------------|
| RT   | Room temperature |
| HV   | High vacuum |
| GC   | Gas chromatography |
| e.e. | Enantiomeric excess |

(R,R)-MOD-DIOP: (4R,5R)-O-Isopropylidene-2,3-dihydroxy-1,4-bis-[bis-(4-methoxy-3,5-dimethyl-phenyl)phosphino)butane (S,S)-mTol-BPPM: tert-Butyl (2S ,4S)-4-(di-m-tolylphosphino)-2-[(di-m-tolylphosphino)methyl]-1-pyrrolidinecarboxylate (R,R)-3,5-tBu,4-Me-O-DIOP: (2R,3R)-O-Isopropylidene-2,3-dihydroxy-1,4-bis-[bis-(4-methoxy-3,5-ditert-butyl-phenyl)-phosphino]butane (R,R)-3,5-MOR-DIOP: (2R,3R)-O-Isopropylidene-2,3-dihydroxy-1,4-bis-[bis-(3,5-di-N-morpholino-phenyl)phosphino]-butane (R,R)-3,4,5-MeO-DIOP: (2R,3R)-O-Isopropylidene-2,3-dihydroxy-1,4-bis-[bis-(3,4,5-trimethoxy-phenyl)phosphino]butane (R,R)-2-Naphthyl-DIOP: (2R,3R)-O-Isopropyliden-2,3-dihydroxy-1,4-bis-[bis-(2-naphthyl)pbosphino]butane (R,R)-(Cy)$_2$(3,5-tBu,4-MeO)$_2$-DIOP; (2R,3R)-O-Isopropylidene-2,3-dihydroxy-1-(dicyclohexylphospino)-4-[bis-(4-methoxy-3,5-ditert-butyl-phenyl)phosphino]butane (R,R)-(3,5-tBu,4-MeO)$_2$-DIOP: (2R,3R)-O-Isopropylidene-2,3-dihydroxy-1-(diphenylphosphino)-4-[bis-(4-methoxy-3,5-ditert-butyl-phenyl)phospbino]butane (R,R)-(Cy)$_2$(3,5-tBu)$_2$-DIOP: (2R,3R)-O-Isopropylidene-2,3-dihydroxy-1-(dicyclohexylphosphino)-4-[bis-(3,5-ditert-butyl-phenyl)phosphino]butane (S,S)-MOD-BPPM: tert-Butyl (2S,4S)4-[bis-(4-methoxy-3,5-dimethyl-phenyl)phosphino]-2-[bis-(4-methoxy-3,5-dimethyl-phenylphosphino)methyl]-1-pyrrolidinecarboxylate (S,S)-3,5-tBu-BPPM: ter-Butyl (2S,4S)-4-[bis-(3,5-ditert-butyl-phenyl)phosphino]-2-[bis-(3,5-ditert-butyl-phenylphosphino)methyl]-1-pyrrolidinecarboxylate (S,S)-(3,5-tBu)$_2$(Ph)$_2$-BPPM: tert-Butyl (2S,4S)-4-[diphenyl)phosphino]-2-[bis-(3,5-ditert-butyl-phenylphosphino)methyl]-1-pyrrolidinecarboxylate (S,S)-3,5-tBu,4-MeO-BPPM: tert-Butyl (2S,4S)-4-[bis-(4methoxy-3,5-ditert-butyl-phenyl)phosphino]-2-]bis-(4-methoxy-3,5-ditert-butyl-phenylphosphino)methyl]-1-pyrrolidinecarboxylate Hexabase: 1-(4-Methoxybenzyl)-3,4,5,6,7,8-hexahydro-isoquinoline (S)-Octabase: (S)-1-[4-Methoxy-benzyl]-1,2,3,4,5,6,7,8-octahydro-isoquinoline All temperatures are given in degrees Celsius.

EXAMPLE 1

In a glove box (O$_2$ content<1 ppm) 13.4 mg (0.020 mmol) of [IrCl(COD)]$_2$ and 32.2 mg 0.044 mmol of (R,R)-MOD-DIOP as the chiral ligand were dissolved in 4 ml of methanol in a 35 ml autoclave having a glass insert. After the addition of 59.1 mg (0.16 mmol) of Bu$_4$N$^+$I$^-$ and stirring for 30 min. 0.343 g (1.0 mmol) of 1-(4-methoxybenzyl)-3,4,5,6,7,8-hexahydro-isoquinoline tetrafluoroborate and 4 ml of toluene were added to this catalyst solution. Then, the autoclave was sealed and the hydrogenation was carried out while stirring at 25° and under a pressure of 100 bar of hydrogen for 44 hours. The yellow hydrogenation solution was evaporated on a rotary evaporator at 40°/20 mbar. With a complete conversion the residue consisted of 90% (S)-octabase with an e.e. of 61% according to HPLC analysis (column- ChiralPAK AD, eluent: 10% ethanol and 0.2% triethylamine in hexane) and GC analysis (as the amide of (−)-camphanic acid, column: OV-240 OH 15 m).

EXAMPLES 1.1–1.10

The hydrogenation was carried out in a manner analogous to Example 1 using the chiral ligands set forth in Table 1.

TABLE 1

| Ex. | Chiral ligand | % Select. to octabase | % e.e. (config.) |
|---|---|---|---|
| 1.1 | (R,R)-MOD—DIOP (a) | 94 | 60 (S) |
| 1.2 | (R,R)-MOD—DIOP (c) | 85 | 51 (S) |
| 1.3 | (R,R)-MOD—DIOP (d) | 91 | 57 (S) |
| 1.4 | (R,R)-MOD—DIOP (e) | 65 | 61 (S) |
| 1.5 | (R,R)-MOD—DIOP (f) | 95 | 58 (S) |
| 1.6 | (R,R)-MOD—DIOP (g) | 97 | 63 (S) |
| 1.7 | (R,R)-MOD—DIOP (h) | 53 | 32 (S) |
| 1.8 | (R,R)-MOD—DIOP (i) | 55 | 28 (S) |

TABLE 1-continued

| Ex. | Chiral ligand | % Select. to octabase | % e.e. (config.) |
|---|---|---|---|
| 1.9 | (R,R)-3,5-tBu—DIOP | 75 | 84 (S) |
| 1.10 | (R,R)-3,5-iProp-4-MeO—DIOP | 69 | 81 (S) |

(a) Addition of 0.04 mmol of phthalimide in place of Bu$_4$N$^+$I$^-$; (c) addition of 1.0 mmol of Et$_3$N; (d) addition of 1.0 mmol of NaOAc; (e) THF as the solvent; (f) DMF as the solvent; (g) solvent: MeOH 4 ml/toluene 4 ml/CO$_2$ 1.3 g; (h) solvent: THF 1 ml/CO$_2$ 12.0 g 45° C.; (i) solvent 12.1 g CO$_2$, 45° C.

EXAMPLE 2a.1–2a.17

Example 2a.1 is described in detail for the Examples in Table 2a. Examples 2a.2 to 2a.17 were carried out analogously.

In a glove box 1.01 mg (0.0015 mmol) of [IrCl(COD)]$_2$ and 3.5 mg (0.0033 mmol) of (R,R)-3,5-tBu-DIOP as the chiral ligand were dissolved in 18 ml of methanol in a 185 ml autoclave. After the addition of 4.3 mg (0.012 mmol) of Bu$_4$N$^+$I$^-$ and stirring for 30 min. 2.12 g (6.0 mmol) of hexabase hydrogen sulphate, 77.7 mg (0.6 mmol) of diisopropylethylamine and 18 ml of toluene were added to this catalyst solution. Then, the autoclave was sealed and the hydrogenation was carried out while stirring at 80° C. and under a pressure of 40 bar of hydrogen for 4–6 hours. The yellow hydrogenation solution was evaporated on a rotary evaporator. With a complete conversion the residue consisted of 95% (S)-octabase with an e.e. of 80% according to HPLC and GC.

TABLE 2a

| Ex. | Chiral ligand | Select. to octabase | % e.e. (config.) |
|---|---|---|---|
| 2a.1 | (R,R)-3,5-tBu,4-MeO—DIOP | 95 | 80 (S) |
| 2a.2 | (R,R)-3,5-tBu—DIOP | 97 | 80 (S) |
| 2a.3 | (R,R)-3,5-Ipr,4-MeO—DIOP | 94 | 80 (S) |
| 2a.4 | (R,R)-MOD—DIOP | 95 | 52 (S) |
| 2a.5 | (R,R)-2-Naphtyl-DIOP | 98 | 24 (S) |
| 2a.6 | (R,R)-3,5-MOR—DIOP | 94 | 45 (S) |
| 2a.7 | (R,R)-3,4,5-MeO—DIOP | 90 | 39 (S) |
| 2a.8 | (R,R)-DIOP | 94 | 27 (S) |
| 2a.9 | (R,R)-(Cy)$_2$(3,5-tBu,4-MeO)$_2$—DIOP | 96 | 61 (S) |
| 2a.10 | (R,R)-(3,5-tBu,4-MeO)$_2$—DIOP | 98 | 46 (S) |
| 2a.11 | (R,R)-(Cy)$_2$(3,5-tBu)$_2$—DIOP | 98 | 65 (S) |
| 2a.12 | (S,S)-3,5-Me,4MeO—BPPM | 95 | 46 (S) |
| 2a.13 | (S,S)-mTol-BPPM | 94 | 40 (S) |
| 2a.14 | (S,S)-BPPM | 95 | 30 (S) |
| 2a.15 | (S,S)-3,5-tBu—BPPM | 93 | 29 (S) |
| 2a.16 | (S,S)-(3,5-tBu,4-MeO)$_2$(Ph)$_2$—BPPM | 99 | 21 (S) |
| 2a.17 | (S,S)-3,5-tBu,4-MeO—BPPM | 98 | 26 (S) |

EXAMPLES 2b.1–2b.13

The hydrogenation of hexabase hydrogen sulphate was carried out in an analogous manner to Example 1 in the solvents listed in Table 2b (addition of 0.1 mmol of iPr$_2$NEt as the base, conversion 40–100%).

TABLE 2b

| Ex. | Solvent 1 | Solvent 2 | Select. to octabase | % e.e. (config.) |
|---|---|---|---|---|
| 2b.1 | Toluene (4 ml) | MeOH (4 ml) | 84 | 89 |
| 2b.2 | Toluene (4 ml) | MeOH (4 ml) | 72 | 86 |

TABLE 2b-continued

| Ex. | Solvent 1 | Solvent 2 | Select. to octabase | % e.e. (config.) |
|---|---|---|---|---|
| 2b.3 | MeOH (8 ml) | H$_2$O (0.2 ml) | 77 | 84 |
| 2b.4[a)] | MeOH (3 ml) | CO$_2$ (6 g) | 80 | 78 |
| 2b.5 | 2-BuOH (8 ml) | | 86 | 67 |
| 2b.6 | THF (8 ml) | H$_2$O (0.2 ml) | 81 | 66 |
| 2b.7 | MeOH (4 ml) | CH$_2$Cl$_2$ (4 ml) | 91 | 65 |
| 2b.8 | THF (8 ml) | | 90 | 63 |
| 2b.9 | THF (4 ml) | CH$_2$Cl$_2$ (4 ml) | 75 | 56 |
| 2b.10 | AcOEt (8 ml) | | 76 | 54 |
| 2b.11 | iPrOH (8 ml) | | 49 | 53 |
| 2b.12 | Toluene (4 ml) | iPrOH (4 ml) | 57 | 49 |
| 2b.13 | Toluene (8 ml) | | 56 | 47 |

[a)] 60°, 65 h, 220 bar total pressure

EXAMPLES 3.1–3.3

The hydrogenation of 1-(4-methoxybenzyl)-3,4,5,6,7,8-hexahydro-isoquinoline hexafluorophosphate with the chiral ligands listed in Table 4 was carried out in an analogous manner to Example 1.

TABLE 3

| Ex. | Cat. | Chiral ligand | % Select. to octabase | % e.e. (config.) |
|---|---|---|---|---|
| 3.1 | [Ir] | (R,R)-MOD—DIOP | 90 | 60 (S) |
| 3.2 | " | (R,R)-MOD—DIOP (a) | 81 | 48 (S) |
| 3.3 | " | (R,R)-MOD—DIOP (b) | 62 | 62 (S) |

(a) No addition of BU$_4$N$^+$I$^-$; (b) THF as the solvent.

EXAMPLE 4

In a glove box (O$_2$ content<1 ppm) 9.9 mg of (0.020 mmol) [Ir(COD)$_2$]BF$_4$ and 16.1 mg (0.022 mmol) of (R,R)-MOD-DIOP as the chiral ligand were dissolved in 4 ml of THF in a 35 ml autoclave having a glass insert and stirred for 30 minutes. After the addition of 29.5 mg (0.08 mmol) of Bu$_4$N$^+$I$^-$ and stirring for 15 minutes. 0.34 g (1.0 mmol) of 1-(4-methoxybenzyl)-3,4,5,6,7,8-hexahydro-isoquinoline bisulphate, 4 ml of THF and 0.5 ml of water were added, the autoclave was sealed and the hydrogenation was carried out while stirring at 25° and under a pressure of 100 bar of hydrogen for 20 h. The yellow hydrogenation solution was evaporated on a rotary evaporator at 40°/20 mbar. With a complete conversion the residue consisted of 67% (S)-octabase with an e.e. of 71% according to HPLC analysis and GC analysis.

EXAMPLE 5

The experiment was carried out in a manner analogous to Example 4, but 25.8 mg (0.08 mol) of Bu$_4$N$^+$Br$^-$ were used in place of Bu$_4$N$^+$I$^-$. With a complete conversion the residue consisted of 65% (S)-octabase with an e.e. of 66% according to HPLC analysis and GC analysis.

EXAMPLE 6

The experiment was carried out in a manner analogous to Example 4, but no tetrabutylammonium iodide was added. With a complete conversion the residue consisted of 87% (S)-octabase, e.e.=56% according HPLC analysis and GC analysis.

EXAMPLE 7

27.34 g (100 mmol) of N-(2-cyclohex-1-enylethyl)-2-(4-methoxyphenyl)acetamide were placed in 30 ml of toluene in a 350 ml four-necked sulphonation flask. 4.73 ml (51 mmol) of distilled phosphorus oxychloride were dosed in at 80° in an inert gas atmosphere using a motorised piston burette within 60 minutes. The solution was left to react for: 1 hour at 80°, thereafter 2 hours at 90° and finally for a further 1 hour at 100°. The reaction mixture contained the dissolved crude Bishler-Napieralsky reaction product 1-(4-methoxybenzyl)-3,4,5,6,7,8-hexahydroisoquinoline of formula II in the form of a salt mixture consisting of HCl and diverse phosphoric acids.

EXAMPLE 8

20.2 g (20 mmol) of 97% sulphuric acid were added dropwise to the reaction mixture, prepared in Example 7, in toluene at 20° in an inert gas atmosphere within 30 minutes, with gaseous hydrochloric acid evolving. The toluene was subsequently distilled off in a water-jet vacuum. The residue was dissolved in 250 ml of isopropanol. After crystallization at 0° for 18 hours the crystallizate was filtered off under suction and rinsed with ice-cold isopropanol. After drying in a water-jet vacuum there were obtained 32.4 g of 1-(4-methoxybenzyl)-3,4,5,6,7,8-hexahydro-isoquinoline hydrogen sulphate, m.p.=186°–7°. Analysis:

| | C | H | N | S | |
|---|---|---|---|---|---|
| Calc: | 57.77 | 6.56 | 3.96 | 9.07 | % |
| Found: | 57.39 | 6.49 | 3.97 | 9.14 | % |

EXAMPLE 9

1-(4-Methoxybenzyl)-3,4,5,6,7,8-hexahydro-isoquinoline perchlorate with m.p. 128°–131° was isolated analogously to Example 8.

EXAMPLE 10

160 ml of ethyl acetate and a solution of 10.98 g (100 mmol) of sodium fluoroborate dissolved in 40 ml of water were added in succession to the reaction mixture, prepared in Example 7, in toluene at RT in an inert gas atmosphere. After stirring for 10 minutes the aqueous phase was separated and the organic phase was concentrated carefully in a vacuum. The residue was dried azeotropically twice with 100 ml of ethyl acetate in a vacuum and subsequently dissolved in 50 ml of ethyl acetate in an inert gas atmosphere. After crystallization. at 0° for 8 hours the product was filtered off under suction and rinsed with 25 ml of ethyl acetate. After drying at 40° in a water-jet vacuum there were obtained 28.1 g of 1-(4-methoxybenzoyl)-3,4,5,6,7,8-hexahydro-isoquinoline tetrafluoroborate, m.p.=97°–8°.

EXAMPLE 11

1-(4-Methoxybenzyl)-3,4,5,6,7,8-hexahydro-isoquinoline hexafluorophosphate, m.p.=161°–162°, was isolated analogously to Example 10.

EXAMPLE 12

1-(4-Methoxybenzyl)-3,4,5,6,7,8-hexahydro-isoquinoline picrate, m.p. 131°–134°. was isolated analogously to Example 10.

EXAMPLE 13

1-(4-Methoxybenzyl)-3,4,5,6,7,8-hexahydro-isoquinoline phthalate, m.p. 116°–120°, was isolated analogously to Example 10.

EXAMPLE 14

A 2 l stirring autoclave was charged while gassing with argon with 148.45 g (420 mmol) of hexabase hydrogen sulphate, 467 ml of methanol, 507 ml of toluene and 4.25 ml of triethylamine and sealed. After replacement of the air atmosphere with hydrogen a catalyst solution consisting of 14.1 mg (0.021 mmol) of [IrCl(COD)]$_2$, 43.8 mg (0.0462 mmol) of (R,R)-3,5-tBu-DIOP and 62.1 mg (0.168 mmol) of Bu$_4$N$^+$I$^-$ in 40 ml of ethanol was allowed to flow in from a catalyst addition vessel. The hydrogenation was carried out at 80° and under a hydrogen pressure of 30 bar for 15 hours. Then, the autoclave was emptied and the hydrogenation solution was evaporated. The residue was dissolved in water, extracted with 200 ml of tert.butyl methyl ether and then treated with an excess of sodium hydroxide solution and with hexane. The hexane phase was separated, washed neutral and evaporated on a rotary evaporator. With a complete conversion the residue (104.9 g) consisted of 93.0% (S)-octabase with an e.e. of 78.1% according to HPLC and GC. The e.e. enrichment was achieved by crystallization of the 1:1 salt of the (S)-octabase with L-(+)-mandelic acid from water. This light beige crystalline material (138.2 g, 81% yield) was treated with an excess of sodium hydroxide solution and with hexane. The hexane phase was washed neutral and evaporated. The resulting (S)-octabase (86.2 g, 80% yield) had a content of 98.0% and an e.e. of 98.6%.

EXAMPLE 15

In a glove box 6.72 mg (0.010 mmol) of (IrCl(COD)]$_2$ and 20.8 mg (0.022 mmol) of (R,R)-3,5-tBu-DIOP as the chiral ligand were dissolved in a mixture of 4 ml of methanol and 2 ml of toluene in a 35 ml autoclave having a glass insert. After the addition of 25.8 mg (0.08 mmol) of Bu$_4$N$^+$I$^-$ and stirring for 30 minutes. 345 mg (1.0 mmol) of hexabase oxalate and 2 ml of toluene were added to this catalyst solution. Then, the autoclave was sealed and the hydrogenation was carried out while stirring at 25° and under a pressure of 100 bar of hydrogen for 18 hours. The yellow hydrogenation solution was evaporated on a rotary evaporator. With a conversion of 99% the residue consisted of 65% (S)-octabase with an e.e. of 70% according to HPLC and GC.

EXAMPLE 16

The hydrogenation of 345 mg (1.0 mmol) of hexabase oxalate was carried out in a manner analogous to Example 15, but with addition of di-isopropylethylamine. With a conversion of 921% The residue consisted of 60% (S)-octabase with an e.e. of 75% according to HPLC and GC.

EXAMPLE 17

The hydrogenation of 345 mg (1.0 mol) of hexabase oxalate was carried out in a manner analogous to Example 15, but with addition of di-isopropylethylamine at a temperature of 80° C. With a conversion of 100% the residue consisted of 86% (S)-octabase with an e.e. of 68% according to HPLC and GC.

We claim:

1. A process for the manufacture of optically active (R)- or (S)- 1-(4-methoxy-benzyl)-1,2,3,4,5,6,7,8-octahydro-isoquinoline adducts of the formula

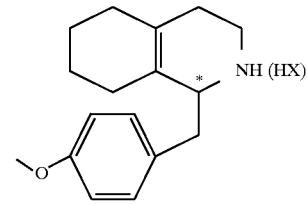

wherein
HX is a mineral acid from the group of HBF$_4$, H$_2$SO$_4$, HPF$_6$, HBr, HI, HCl, HSbF$_6$ or HClO$_4$, or a strong organic acid from the group of C$_{1-8}$-alkylSO$_3$H, picric acid, formic acid, a lower alkylcarboxylic acid or arylcarboxylic acid or a dicarboxylic acid, which process comprises asymmetrically hydrogenating a compound of the formula

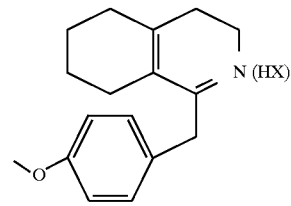

in the presence of a complex consisting of optically active diphosphine ligand with iridium.

2. A process according to claim 1, wherein the asymmetric hydrogenation of compounds of formula II is carried out in the presence of a base as an additive.

3. A process according to claim 1, wherein the asymmetric hydrogenation of compounds of formula II is carried out in the presence of at least one of an optically active, cationic, anionic or neutral iridium-diphosphine complex of the following formulas

| | |
|---|---|
| [Ir(Y)(L$_n$)]$^+$A$^-$ | III-a |
| [Ir(Y)(L$_n$)B] | III-b |
| ([Ir(Y)(B)$_4$])$_o^-$M$^{r+}$ | III-c |
| [IrH(Y)(B)$_2$]$_2$ | III-e |
| [Ir(Y)(B)$_3$]$_2$ | III-f |
| [Ir(B)$_3$(Y)] | III-g | wherein
L is a neutral ligand;
A is an anion of an oxygen acid or complex acid;
B is an anionic coordinating ligand;
n is 0, 1 or 2;
o is 1 or 2;
r is 1 or 2;
M$^+$ is alkali, alkaline earth or tetrasubstituted ammonium:
Y is a chiral diphosphine ligand of the formula

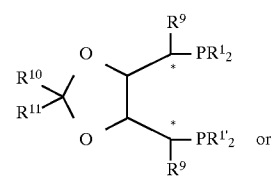

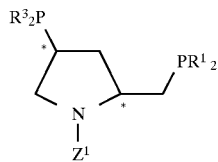

in which
- $R^1$, $R^{1'}$ each independantly are $C_{3-8}$-cycloalkyl, aryl or heteroaryl or together with the phosphorus atom are 9-dibenzophospholyl;
- $R^2$ is $C_{1-8}$-alkyl, $C_{3-8}$-cycloalkyl, aryl or aralkyl; or two $R^2$'s together in the same molecule can form a 5- to 8-membered ring;
- $R^3$ is $C_{1-8}$-alkyl, heteroaryl, aryl, $C_{3-8}$-cycloalkyl or aralkyl;
- $R^9$, $R^{10}$, $R^{11}$ each independently are hydrogen, $C_{1-8}$-alkyl, halogenated $C_{1-8}$-alkyl, $C_{3-8}$-cycloalkyl, aryl or aralkyl; or $R^{10}$ and $R^{11}$ together can form a 5- to 8-membered ring; and
- Z1 is hydrogen, $C_{1-8}$-alkyl, aralkyl, $-CO_2R^2$, $-CONR^2{}_2$, $-SO_2R^{10}$, $-POR_2{}^{10}$ or $-COR^3$.

4. A process for the manufacture of a compound of formula I in accordance with claim 1, wherein the asymmetric hydrogenation is carried out in a temperature range of 10° C. to 200° C., under a pressure of 1 to 250 bar and using a substrate to catalyst ratio of 20–80000.

5. A process according to claim 2, wherein bases from the group of carboxylic acid salts, carbonates, primary, secondary or tertiary amines, imides, alkalialkoholates, selected from sodium methylate, and sodium hydroxide are used as the additives.

6. A process according to claim 5, wherein secondary or tertiary amines are used as the bases.

7. A process according to claim 5, wherein the amount of additives from the group of carboxylic acid salts and primary, secondary or tertiary amines is in a range of 0.001–100 mol equivalents based on the compound of formula II.

8. 1-(4-methoxy-benzyl)-3,4,5,6,7,8-hexahydro-isoquinoline hydrogen sulphate.

9. 1-(4-methoxy-benzyl)-3,4,5,6,7,8-hexahydro-isoquinoline hexafluorophosphate.

10. 1-(4-methoxy-benzyl)-3,4,5,6,7,8-hexahydro-isoquinoline tetrafluorborate.

11. 1-(4-methoxy-benzyl)-3,4,5,6,7,8-hexahydro-isoquinoline phthalate.

12. 1-(4-methoxy-benzyl)-3,4,5,6,7,8-hexahydro-isoquinoline perchlorate.

* * * * *